United States Patent
Hodgson et al.

(10) Patent No.: US 11,236,465 B2
(45) Date of Patent: Feb. 1, 2022

(54) WOOL TREATMENT PROCESS AND PRODUCTS

(71) Applicant: Woolchemy NZ Limited, Upper Hutt (NZ)

(72) Inventors: Alexandra Hodgson, Lincoln (NZ); Paul Middlewood, Christchurch (NZ); Mohammad Azam Ali, Dunedin (NZ); Derelee Potroz-Smith, Wellington (NZ)

(73) Assignee: WOOLCHEMY NZ LIMITED, Upper Hutt (NZ)

( * ) Notice: Subject to any disclaimer, the term of this patent is extended or adjusted under 35 U.S.C. 154(b) by 0 days.

(21) Appl. No.: 15/562,983

(22) PCT Filed: Apr. 1, 2015

(86) PCT No.: PCT/IB2015/052394
§ 371 (c)(1),
(2) Date: Sep. 29, 2017

(87) PCT Pub. No.: WO2016/156922
PCT Pub. Date: Oct. 6, 2016

(65) Prior Publication Data
US 2018/0112353 A1  Apr. 26, 2018

(51) Int. Cl.
*D06M 11/38* (2006.01)
*D06M 11/50* (2006.01)
*D06M 13/144* (2006.01)
D06M 101/12 (2006.01)
A61F 13/53 (2006.01)

(52) U.S. Cl.
CPC ............ *D06M 11/38* (2013.01); *D06M 11/50* (2013.01); *D06M 13/144* (2013.01); *A61F 2013/530357* (2013.01); *D06M 2101/12* (2013.01)

(58) Field of Classification Search
CPC .... D06M 11/38; D06M 11/50; D06M 13/144; D06M 2101/12; A61F 2013/530357
See application file for complete search history.

(56) References Cited

U.S. PATENT DOCUMENTS

| 5,136,761 | A | * | 8/1992 | Sternlieb | D06C 29/00 28/104 |
| 6,099,588 | A | * | 8/2000 | McDevitt | D06M 11/38 435/263 |
| 6,544,548 | B1 | | 4/2003 | Siller-Jackson et al. | |
| 2007/0207111 | A1 | | 9/2007 | Nomura et al. | |

FOREIGN PATENT DOCUMENTS

| CN | 102031695 A | | 4/2011 | | |
| EP | 0134267 | * | 8/1983 | | D06M 16/00 |
| JP | 408238162 | * | 9/1996 | | A47G 27/02 |
| WO | 1994025629 | | 11/1994 | | |
| WO | 2005124011 | | 12/2005 | | |
| WO | 2005124013 | | 12/2005 | | |
| WO | 2007017668 A | | 2/2007 | | |
| WO | 2013043062 | | 3/2013 | | |
| WO | WO 2013/043062 | * | 3/2013 | | C08H 1/06 |

OTHER PUBLICATIONS

Morita K., Derwent 2008-M21788, 2008.*

* cited by examiner

*Primary Examiner* — Amina S Khan
(74) *Attorney, Agent, or Firm* — Arent Fox LLP (57) ABSTRACT

The present invention relates to a wool treatment process and to a wool product produced by the wool treatment process. In particular, the invention relates to a wool treatment process that produces a wool product with increased absorbency properties and to a wool product that has increased absorbency properties.

11 Claims, 8 Drawing Sheets

Absorbency was evaluated by contact angle (θ) using a goniometer measurement technique

Figure 10 – Control Sample

Figure 11 – 8 minute sample

Figure 12 – 10 minute sample

Figure 13 – 12 minute sample

Figure 14 – 14 minute sample

Figure 15 – 16 minute sample

Figure 16 – 18 minute sample

Figure 17 – 20 minute sample

WOOL TREATMENT PROCESS AND PRODUCTS

CROSS REFERENCE TO RELATED APPLICATIONS

This application is a U.S. National Phase of International Patent Application PCT/IB2015/052394, filed Apr. 1, 2015, the content of which is hereby incorporated by reference in its entirety.

FIELD OF THE INVENTION

The present invention relates to a wool treatment process and to a wool product produced by the wool treatment process. In particular, the invention relates to a wool treatment process that produces a wool product with increased absorbency properties and to a wool product that has increased absorbency properties.

BACKGROUND OF THE INVENTION

One area of concern for today's environmental and health conscious consumer is the volume of non-biodegradable waste that is generated from disposable products such as diapers, diaper liners and incontinence pads. Disposable diapers contain chemical compounds such as super-absorbent polymers, polypropylene, adhesives, elastics and pulp. Large volumes of these products end up in landfills, and take long periods of time to degrade, causing long-term harm to the environment.

Many consumers are looking for alternatives to currently available products of this type. Consumers are looking in particular for odour-free, chemical-free, biodegradable and environmentally friendly products that are reasonably priced and still provide the absorbency needed for such products.

Absorbent products are needed in other situations such as in domestic, commercial and industry cleaning and when dealing with fluid spills, as well as for personal hygiene and health products, such as diapers, nappies, as nursing pads and wound and surgical dressings. Also, there is a need for absorbent clothing for sports, outdoor activities and general everyday fashion items.

Wool is a natural product which has many characteristics that make it a product or product ingredient of choice for today's environmental and health conscious consumers. Important characteristics of wool are that it is renewable, biodegradable, non-allergenic, breathable, a natural insulator, durable, elastic and washable. However, wool as an untreated natural product is hydrophobic with very limited absorbency.

A need therefore exists to provide an absorbent material that is reasonably priced, sourced from a naturally occurring and renewable source and acceptable to the increasing numbers of environmental and health conscious consumers. A further need exists to at least provide a useful alternative to currently available absorbent materials.

SUMMARY OF THE INVENTION

In a first aspect, the present invention provides a process for treating a wool substrate comprising:
a first reaction step of treating the wool substrate with an alcohol and alkali reaction mixture for a reaction time of between about 5-60 minutes; and
a second reaction step of treating the resulting wool substrate obtained from the first reaction step with an aqueous oxidizing agent mixture.

In one embodiment the wool substrate used in the first reaction step is a chemically untreated nonwoven wool substrate.

In another embodiment the wool substrate used in the first reaction step is a chemically untreated knop-infused nonwoven substrate.

In another embodiment the wool substrate used in the first reaction step is selected from (i) a needle punched or (ii) spunlaced (hydroentangled) wool nonwoven comprising layered spunbonded or carded wool fibres.

In another embodiment the wool substrate has a density of between about 100-1000 grams per square meter. In one embodiment the wool substrate has a density of between about 200-600 grams per square meter.

In another embodiment the wool substrate used in the first reaction step comprises loose wool fibres, preferably raw but scoured untreated wool fibres.

In one embodiment the alcohol is selected from methanol, ethanol, propanol, butanol or mixtures thereof.

In one embodiment the alkali is selected from potassium hydroxide or sodium hydroxide or mixtures thereof.

In one embodiment the alkali concentration in the alcohol mixture is between about 0.5-5%. Preferably the alkali concentration in the alcohol mixture is between about 1-2%. More preferably the alkali concentration in the alcohol mixture is about 1.5%.

In one embodiment the oxidizing agent is hydrogen peroxide.

In one embodiment the oxidizing agent concentration in the aqueous mixture is between about 0.5-5%. Preferably the oxidizing agent concentration in the aqueous mixture is about 1-2%. More preferably the oxidizing agent concentration in the aqueous mixture is about 2.0%.

In one embodiment the reaction time of the first reaction step is between about 5-30 minutes. More preferably the reaction time of the first reaction step is between about 10-30 minutes. Where the wool substrate is a nonwoven wool substrate, the preferred reaction time of the first reaction step is about 10 minutes. Where the wool substrate comprises loose wool fibres, the preferred reaction time of the first reaction step is about 12 to 14 minutes.

In one embodiment the reaction time of the second reaction step is between about 30-180 minutes. Preferably, the reaction time of the second reaction step is between about 30-120 minutes. More preferably the reaction time of the second reaction step is between about 30-90 minutes. Most preferably the reaction time of the second reaction step is about 60 minutes.

In one embodiment, the process of the invention is carried out with a fibre to liquor ratio of 1:10 to 1:40.

In a second aspect, the present invention provides a wool product obtained by the process defined above, wherein the wool product has absorbency properties at least 800% greater than an untreated wool substrate.

In one embodiment the wool product has absorbency properties at least 1000% greater than the untreated wool substrate. In another embodiment the wool product has absorbency properties at least greater than 1200% greater than an untreated wool substrate.

Where the wool substrate comprises loose wool fibres, the treated wool has absorbency properties at least 1500% greater that the untreated loose wool fibres, and up to 2400% greater that the untreated loose wool fibres.

In one embodiment the wool product is further used in one or more products requiring a material with absorbent properties. Such products include personal hygiene products such as diapers, diaper liners, nappies and the like, wound dressings or surgical dressings and the like, chemical spill or clean up products and the like, and sporting, outdoor and general everyday fashion garments.

This summary of the invention broadly describes the features and advantages of certain embodiments of the invention. Further features and advantages will be described in the detailed description of the invention that follows.

Novel features that are believed to be characteristic of the invention will be better understood from this detailed description when considered in connection with the accompanying figures and examples. However, the accompanying figures and examples are intended to help illustrate the invention or assist with understanding the invention, and are not intended to define or limit the scope of the invention.

DETAILED DESCRIPTION OF THE INVENTION

Prior to setting forth the invention in detail, it may be helpful to provide definitions of certain terms to be used in this specification.

The term "about" as used in connection with a referenced numeric indication means the referenced numeric indication plus or minus up to 10% of that referenced numeric indication. For example, the language "about 50" units covers the range of 45 units to 55 units.

The term "wool substrate" as used includes a raw wool substrate, such as raw sheep's wool, loose wool fibres, including raw untreated wool fibres, cashmere, mohair, angora, 100% crossbred wool; merino wool, a raw wool substrate that has been washed and dried; a raw wool substrate that has been washed, dried and has been needled into a nonwoven web or pad. The wool substrate preferably has a density of between 100-1000 grams per square metre, such as 100 gsm, 200 gsm, 400 gsm, 600 gsm, 800 gsm or 1000 gsm.

The wool treatment process of the present invention produces a wool product with increased absorbency properties, making the wool produced by the treatment process of the present invention a useful absorbent product or a useful ingredient for products that require absorbency, such as diapers, diaper liners, wound and surgical dressing, incontinence pads or the like, as well as for activewear garments used in sports, outdoor activities and everyday activities.

In a first aspect, the present invention provides a process for treating a wool substrate comprising:
  a first reaction step of treating the wool substrate with an alcohol and alkali reaction mixture for a reaction time of between about 5-60 minutes; and
  a second reaction step of treating the resulting wool substrate obtained from the first reaction step with an aqueous oxidizing agent mixture.

In one embodiment the alkali concentration in the alcohol mixture is about 0.5-5%. Preferably the alkali concentration in the alcohol mixture is about 1-2%. More preferably the alkali concentration in the alcohol mixture is about 1.5%.

In one embodiment the alcohol and alkali reaction mixture comprises a mixture of ethanol and potassium hydroxide.

In one embodiment, the alcohol and alkali reaction mixture comprises about 1.5% sodium hydroxide (for example, 2.8 kg of sodium hydroxide in 217 litres of ethanol). In another embodiment, the alcohol and alkali reaction mixture comprises about 1.5% potassium hydroxide (for example 3.0 kg of potassium hydroxide in 200 litres of 96% ethanol).

In one embodiment the oxidizing agent concentration in the aqueous mixture is about 0.5-5%. Preferably the oxidizing agent concentration in the aqueous mixture is about 1-2%. More preferably the oxidizing agent concentration in the aqueous mixture is about 2.0%.

In one embodiment the oxidizing agent is hydrogen peroxide.

In one embodiment, the aqueous oxidizing agent mixture comprises 2% hydrogen peroxide (for example 9 litres 50% hydrogen peroxide in 224 litres of water).

In one embodiment the reaction time of the first reaction step is between about 5-30 minutes. More preferably the reaction time of the first reaction step is between about 10-30 minutes. Where the wool substrate is a nonwoven wool substrate, the preferred reaction time of the first reaction step is about 10 minutes. Where the wool substrate comprises loose wool fibres, the preferred reaction time of the first reaction step is about 12-14 minutes.

In one embodiment the reaction time of the second reaction step is between about 30-180 minutes. Preferably, the reaction time of the second reaction step is between about 30-120 minutes. More preferably the reaction time of the second reaction step is between about 30-90 minutes. Most preferably the reaction time of the second reaction step is about 60 minutes.

In one embodiment, the process of the invention is carried out with a fibre to liquor ratio of 1:10 to 1:40. The preferred ratio will depend on the nature and amount of the wool substrate being treated, the size of the reaction vessel and such like.

In one embodiment, the reagents (in particular the alcohol) are recovered and recycled where possible, reducing cost and harmful waste.

In another embodiment the process includes the further step of rinsing the wool substrate with water between the first and second reaction steps.

In another embodiment the process includes the further step of rinsing the wool product with water after the second reaction step.

In another embodiment the process includes the further step of rinsing and then drying the wool product after the second reaction step.

Preferably, the wool substrate comprises 100% crossbred wool (approximately 35-42 micron).

The process is preferably applied to a non-woven wool substrate.

In one embodiment of the invention, the non-woven wool substrate is 400 grams per square metre (gsm), although the non-woven wool substrate can also be of other densities such as 200 or 600 gsm.

In one embodiment, the non-woven wool substrate is produced in rolls of approximately 1.5 metres by 30 metres, although it will be appreciated that any suitable width and/or length may be used.

In another embodiment the process is applied to a loose wool fibre substrate.

Without wanting to be bound by any theory, it is thought that the process of the present invention is a wet treatment that impacts the entire wool fibre structure (the wool surfaces and also the wool matrix). The wool fibre undergoes relaxation through chemical changes (breaking and reforming the structure of the wool fibre bonds). More specifically, alkaline —OH ions break the disulfide bonds through the interaction of acidic hydrogen atoms next to the sulfur atoms and that allows the wool material to become significantly absorbent.

The treatment process of the present invention produces a highly absorbent wool product, for example a treated wool substrate. In one preferred embodiment, the wool product is able to absorb up to 1200-1500% of its weight in moisture (compared with 30% for wool that has not treated by the process of the present invention). In another preferred embodiment, the wool product is able to absorb up to 2400% of its weight in moisture.

Useful properties of the wool product of the present invention may include: super-absorbent, anti-odour, anti-microbial (by natural wicking of moisture and breathability of the material), chemical-free, synthetic-free and petroleum-free, rash-reducing, fire-retardant, temperature controlling, hypo-allergenic, warm, comfortable, breathable, biodegradable and compostable, renewable and sustainable wool product that may be cut or shaped into any desired shape suitable for a required purpose.

The wool product of the present invention may be used in a variety of applications including domestic, commercial and industrial cleaning products and cleaning accessories, beauty cleaning aids (such as facial masks, exfoliating wipes/gauze, soap dispensers and scrubbing aids), diaper components (such as soaker pads, acquisition layer and nappy liners), toilet training bed pads & booster pads, nursing pads for mothers, incontinence pads and pants, animal toilet pads, pet beds, petroleum and mechanical fluid spills, aids to absorb any fluids exposed to electronic devices, medical devices (such as wound care dressings, surgical gowns, surgical gauze and body warmers), fashion activewear garments for sports, outdoor activities and everyday activities.

Figure 1:
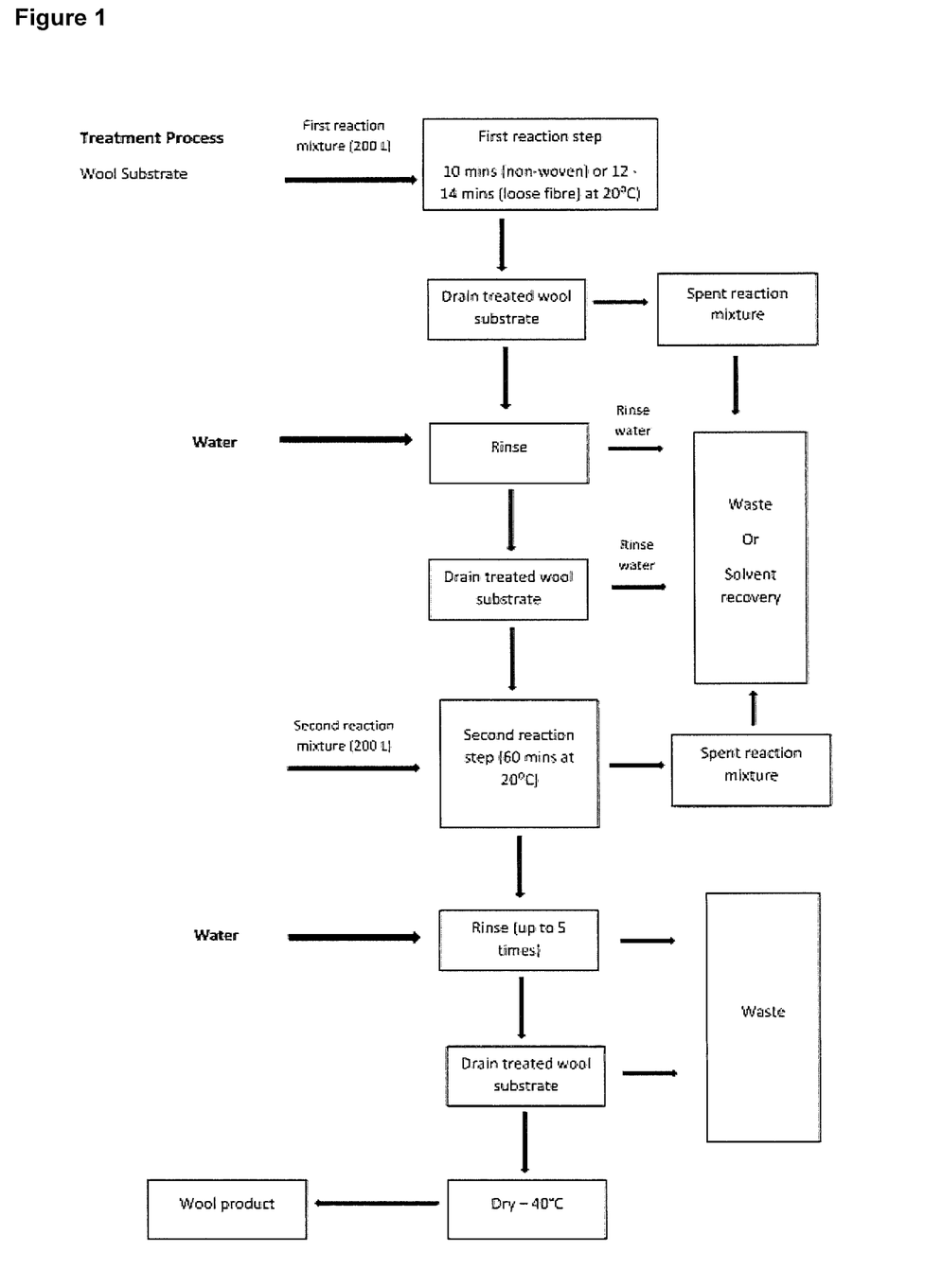
FIG. 1: is a flow diagram of a process for treating wool according to one aspect of the present invention.

A process according to one preferred embodiment of the present invention is shown in FIG. 1 of the accompanying drawings.

In this embodiment of the invention, the treatment process involves preliminary or pre-treatment steps of preparing the first reagent and the second reagent.

Once the reagents are prepared, the treatment process is commenced. Wool, for example a roll of non-woven wool substrate, is treated by immersion into a bath containing the first reaction mixture. The wool substrate is retained in the bath of the first reaction mixture for a predetermined period of time, for example about 5-60 minutes.

The wool substrate is removed from the bath and drained. The first reaction mixture is further processed, to recover ethanol (which may be re-used).

The treated wool substrate is then rinsed using water. Several rinsing cycles can be employed.

In the second reaction step of the treatment process, the wool substrate obtained from the first reaction step is treated by immersion into a bath containing the second reaction mixture. The wool substrate is retained in the bath of the first reagent for a predetermined period of time, for example about 60-180 minutes.

The wool substrate is removed from the bath, drained and rinsed with water. Again, several rinsing cycles can be employed.

After this rinsing, the wool substrate is dried, to produce the treated wool product of the present invention.

Typically, the reagents used in the process of the present invention will be at a temperature of about 20° C. (ie room temperature), and typically the process will be carried out at about 20° C. (ie room temperature).

The invention will now be described with reference to the examples.

EXPERIMENTAL

Example 1—The Reaction Conditions

1) Preparation of 1.5% potassium hydroxide (KOH) in ethanol (EtOH) solution:
3.0 kg of KOH pellets in 200 litres of EtOH or 6.0 kg of KOH in 400 litres EtOH (Preparation of a small quantity with higher concentration was found to be best practice; for example, 3.0 kg in 20 litres, which was then diluted with EtOH appropriately to make the 1.5% KOH solution).
(1a) 20 litres of EtOH was added to a clean container (glass or stainless steel or suitable plastic).
(1b) 3.0 kg of KOH pellets was added slowly into (1a) and mixed until all the KOH pellets were completely dissolved (note: mixing solution/container may generate some heat).

(1c) Then an appropriate amount of EtOH was added into (1a), until a total 1.5% KOH concentration in EtOH was achieved.

2) An appropriate wool substrate(s) was selected (such as 200 gsm, 400 gsm or 600 gsm wool substrate). The total size and weight of the wool substrate was measured and determined.

3) 1.5% KOH in EtOH treatment/processing scheme:

(3a) A suitable dry and clean treatment vessel (preferably glass or stainless steel) was selected.

(3b) An adequate amount of 1.5% KOH in EtOH solution (pre-prepared) was added into the vessel (3a) and handle with care (using appropriate safety equipment and conditions).

(3c) The wool substrate (for example, a 400 gsm wool substrate) was added and immersed completely into the treatment solution consisting of 1.5% KOH in EtOH concentration for 20 minutes (preferably without agitation) at room temperature (20° C.±2° C.)

(3d) The treatment solution was recovered for reuse, or used to treat a second batch or third batch of wool substrate, if practicable.

(3e) The treated wool substrate was then rinsed (preferably, at least 5 times) in reverse osmosis (RO) water at room temperature. The process may include drying the wool substrate prior to applying the hydrogen peroxide ($H_2O_2$) treatment step.

4) Preparation of 2% hydrogen peroxide ($H_2O_2$) solution in water:

Option 1: The total requirement of $H_2O_2$ was calculated and added into the reaction vessel and filled with water until the desired concentration (i.e. 2%) was obtained.

Option 2:

(4.2a) 100 litres of RO water was added to a clean container (glass or stainless steel or suitable plastic).

(4.2b) 1.5 kg of $H_2O_2$ (if 30% already diluted) was added into (4.2a) and mixed at room temperature to make sure the $H_2O_2$ homogeneously dissolved. An appropriate quantity of water was added into (4.2a) to achieve a 2% $H_2O_2$ concentration.

(4.2c) Treatment condition: a total exposure/treatment time 60 minutes at room temperature (20° C.±2) without agitation was preferable. This was followed by rinsing with water at least 5 times prior to drying (using hot air or other ways). It is recommended to not dry over 120° C., which may cause yellowing of the substrate.

Example 2—Optimisation of the Reaction Conditions

100% New Zealand sheep wool matrix (needle punched wool nonwoven substrate) cut into a circular shape and having a 100 mm diameter with a mass of 200 gsm or 400 gsm samples were used as a substrate. Potassium hydroxide (KOH), 97.6% absolute ethyl alcohol (EtOH), hydrogen peroxide and ammonium solution were used for the pre-/post treatment of the wool substrate.

The wool sample was conditioned for 48 hours (20° C., 65% relative humidity) prior to treatment with a formulated treatment solution containing KOH/EtOH at various concentrations e.g. 1%, 1.5% and 2% over diverse time periods e.g. 10 minutes, 20 minutes and 30 minutes. The pre-treatment process using 1% KOH/EtOH was applied to treat 100 mm circular diameter wool samples at room temperature over time periods of 10 minutes, 20 minutes and 30 minutes respectively. The pre-treated sample were then individually treated (i.e. post-treated) with 2% $H_2O_2$ at room temperature over time periods of 60 minutes, 90 minutes, and 120 minutes. Similarly, pre-treatment experiments were conducted to treat wool samples using 1.5%, 2% concentration of KOH/EtOH, followed by post-treatment using $H_2O_2$ solution at the above mentioned conditions. The results are detailed in Table 1 below.

TABLE 1

The variables tested, their concentration and conditions for the treatment of wool substrates (400 gsm and 200 gsm) were as follows.

| Reagents and treatment formulations | Concentration and condition (e.g., time, temperature) |
| --- | --- |
| Concentration of potassium hydroxide in ethanol (KOH/EtOH) | 1%, 1.5%, 2%; at room temperature (~20° C.) |
| Duration of exposure to KOH/EtOH | 10 min, 20 min, 30 min; at room temperature (~20° C.) |
| Duration of exposure to 2% hydrogen peroxide $H_2O_2$ | 60 min, 90 min, 120 min; at room temperature (~20° C.) |

A set of test samples (n=5) for each treatment (pre-treatment and post-treatment) associated with a given treatment formulation and process time were generated for absorbency testing. The water-saline absorbency testing methods selected for evaluation of the untreated (control) and treated wool samples were based on ISO standard ISO 11948:1-1998: total absorbency capacity.

Figure 2:
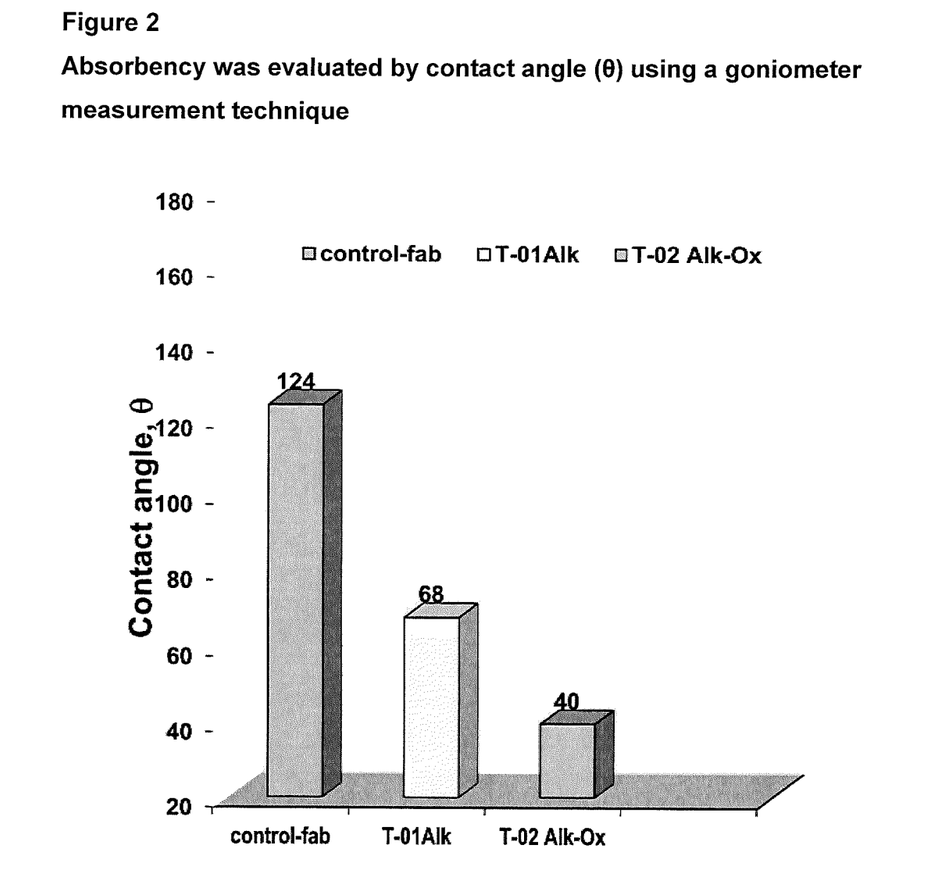
FIG. 2: shows the results of the absorbency testing evaluated by the contact angle (θ) using a goniometer measurement technique. The absorbency was measured after the alkali first reaction step then after the oxidative second reaction step.

All the wool samples (treated and untreated) were conditioned for 48 hours (20° C., 65% relative humidity) prior to the water absorbency efficacy testing (mass changes) in the same environment required by ISO standard (ISO 11948:1-1998). The surface hydrophilicity of the resulting wool product was investigated using a water contact angle meter (KSV CAM101). The absorbency was measured after the alkali first reaction step then after the oxidative second reaction step. Measurements were taken after 30 seconds of contact and an average of 5 measurements were reported. The results of the absorbency testing evaluated by the contact angle (θ) using a goniometer measurement technique are shown in FIG. 2. FTIR (ATR) was employed to investigate the structure-function properties of the wool before during and after treatment. The surface morphology of the wool fiber was analysed via scanning electron microscopy (SEM) images analysis. A water absorbent study was carried out by following a standard method (ISO 11948:1-1998: total absorbency capacity).

The hydrophilicity/absorbency results of the resulting wool product for the 200 gsm substrate are tabulated in Table 2 below.

TABLE 2

Grouped descriptive statistics for water-saline absorbency percentages (200 gsm wool substrates).

| Wool Fabrics (200 GSM) | | | | | | | |
|---|---|---|---|---|---|---|---|
| $H_2O_2$ Exposure (mins) | KOH/EtOH Exposure (mins) | KOH/EtOH Concentration | | | | | |
| | | 1% | | 1.5% | | 2% | |
| | | $\bar{x}$ | s.d | $\bar{x}$ | s.d | $\bar{x}$ | s.d |
| Control | 0 | 356.17% | 0.034 | 443.14% | 0.077 | 467.09% | 0.065 |
| 60 | 10 | 1204.01% | 0.561 | 1411.09% | 0.778 | 1301.33% | 0.253 |
| | 20 | 1227.34% | 5.010 | 1303.33% | 2.110 | 1267.01% | 1.871 |
| | 30 | 1297.92% | 0.887 | 1333.28% | 0.778 | 1252.90% | 2.997 |
| 90 | 10 | 1201.62% | 0.887 | 1312.20% | 1.870 | 1298.12% | 1.112 |
| | 20 | 1192.01% | 2.651 | 1279.90% | 2.531 | 1238.03% | 2.970 |
| | 30 | 1234.17% | 0.887 | 1288.11% | 2.008 | 1201.77% | 3.012 |
| 120 | 10 | 1204.96% | 1.330 | 1298.11% | 0.089 | 1239.01% | 0.778 |
| | 20 | 1167.12% | 1.087 | 1301.06% | 3.103 | 1198.23% | 1.003 |
| | 30 | 1223.98% | 1.003 | 1291.23% | 1.187 | 1276.30% | 2.023 |

It can be seen from these results that the treated wool samples exhibited significant water-saline absorption capacities (approximately 1300% on weight) compared to the control (untreated wool matrix). The treatment of the wool matrix did not modify the physical properties of the wool, such as its flexibility, brittleness, structural integrity and odour. The treated wool product was slightly brighter (whiter) in colour than the untreated wool matrix.

The hydrophilicity/absorbency results of the resulting wool product for the 200 gsm substrate are tabulated in Table 3 below.

TABLE 3

Grouped descriptive statistics for water-saline absorbency percentages (400 gsm wool substrates)

| Wool Fabrics (400 GSM) | | | | | | | |
|---|---|---|---|---|---|---|---|
| $H_2O_2$ Exposure (mins) | KOH/EtOH Exposure (mins) | KOH/EtOH Concentration | | | | | |
| | | 1% | | 1.5% | | 2% | |
| | | $\bar{x}$ | s.d | $\bar{x}$ | s.d | $\bar{x}$ | s.d |
| Control | 0 | 480.07% | 0.066 | 538.54% | 0.032 | 591.19% | 0.037 |
| 60 | 10 | 1241.21% | 0.326 | 1503.17% | 2.929 | 1400.08% | 0.253 |
| | 20 | 1370.13% | 4.120 | 1391.88% | 1.961 | 1356.92% | 1.871 |
| | 30 | 1397.92% | 2.330 | 1406.09% | 0.582 | 1342.03% | 3.734 |
| 90 | 10 | 1319.62% | 0.777 | 1405.36% | 1.526 | 1405.66% | 0.829 |
| | 20 | 1284.31% | 1.881 | 1369.12% | 1.951 | 1328.71% | 3.947 |
| | 30 | 1355.58% | 0.703 | 1365.91% | 1.527 | 1296.33% | 2.553 |
| 120 | 10 | 1334.77% | 0.187 | 1391.65% | 1.069 | 1321.55% | 0.834 |
| | 20 | 1245.25% | 1.369 | 1394.30% | 2.147 | 1279.64% | 0.665 |
| | 30 | 1334.03% | 1.156 | 1396.48% | 1.698 | 1390.06% | 0.198 |

* Total percentage absorbancy capabilities (weight absorbed/original weaight of samples × 100)

It can be seen from the results in Table 3 that the treated wool samples exhibited significant water-saline absorption capacities (approximately 1300% on weight) compared to the control (untreated wool matrix). The treatment of the wool matrix did not modify the physical properties of the wool, such as its flexibility, brittleness, structural integrity and odour. The treated wool product was slightly brighter (whiter) in colour than the untreated wool matrix.

Figure 3A:
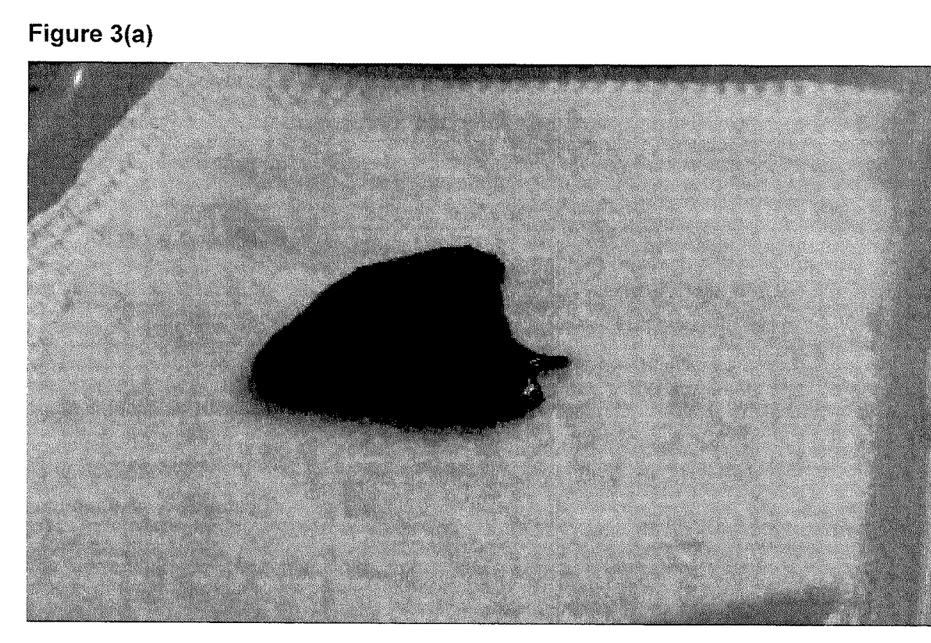
FIGS. 3(a) and 3(b): show photos of the comparative absorbency results of an untreated wool substrate 3(a) compared to a treated wool substrate 3(b) in the presence of an ink sample.
Figure 3B:
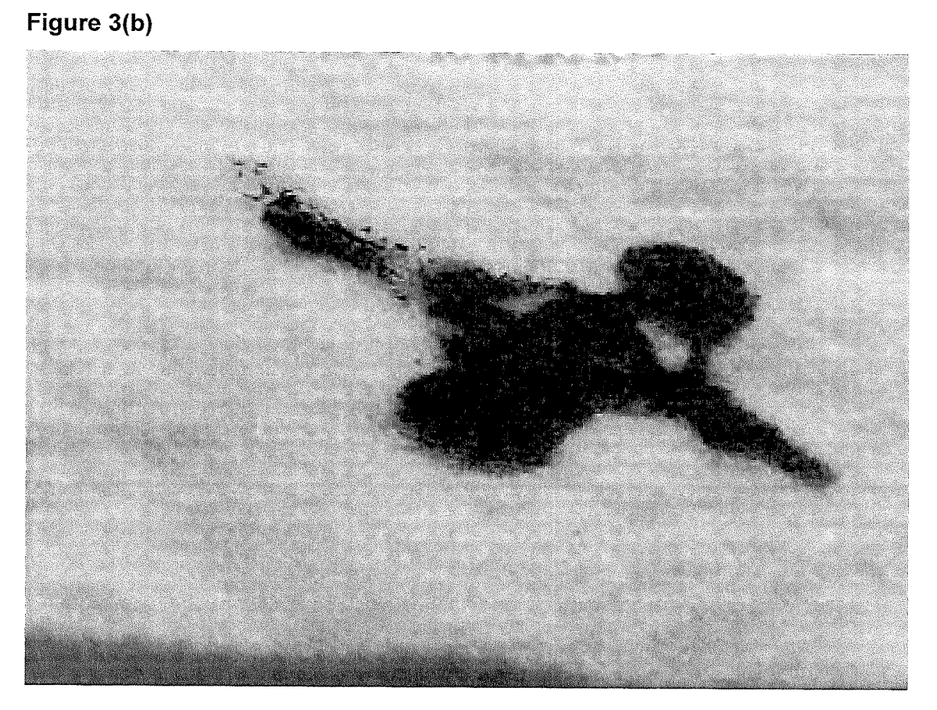

FIGS. 3(a) and 3(b) clearly show the comparative absorbency of an untreated wool substrate in 3(a) compared to a treated wool substrate 3(b) in the presence of an ink sample. FIG. 3(a) shows the hydrophobicity of an untreated wool pad and the ink beading on the surface of the wool substrate. In contrast FIG. 3(b) shows the ink has been readily absorbed into the wool substrate without any beading at all on the surface of the wool substrate.

Example 3—Re-Usability of Reaction Mixtures

A study to determine the reusability of the 1.5% KOH/EtOH reaction mixture was carried out for four reaction/batch cycles. After the third cycle the reaction mixture of 1.5% KOH/EtOH became muddy yellow/orange in colour, which colouration also appeared slightly in the treated wool substrates where a light yellowish wool substrate was exhibited.

The water-saline absorbency percentages are shown in Table 4 below. It can be seen from the results that there were no significant differences observed between the absorbency of the resulting wool substrate from the fresh treatment reaction mixture of KOH/EtOH and resulting wool substrate from the re-used reaction mixture of KOH/EtOH in cycles 1-3. This strongly suggests that the first reaction mixture can be re-used over a number of treatment cycles without compromising the absorbency results obtained. It is also to be appreciated that the EtOH can be recovered by distillation from the reaction mixture.

TABLE 4

Water-saline absorbency percentages and descriptive statistics results that illustrate the reusability of the KOH/EtOH reaction mixture (for an exposure duration of 10 mins) whilst still producing high absorbent wool products for a 400 gsm wool substrate over 4 reaction cycles.

Wool Fabrics (400 GSM)

| $H_2O_2$ Exposure (mins) | KOH/EtOH Exposure (mins) | KOH/EtOH Re-usability cycles | Concentration 1.5% $\overline{X}$ | s.d |
|---|---|---|---|---|
| Control | — | — | 469.20% | 0.277 |
| 60 | 10 | Cycle - 0 (fresh) | 1397.04% | 1.103 |
|  |  | Cycle - 1 | 1347.68% | 1.566 |
|  |  | Cycle - 2 | 1383.74% | 0.695 |
|  |  | Cycle - 3 | 1379.66% | 1.484 |

Example 4—Treatment of Wool Fibre

Wool fibre was supplied from a Hawkes Bay wool scourer. The fibre was scoured strong wool (3/4 Romney breed, second shear) having good colour and low vegetable matter, with an estimated mean fibre diameter in the range 35-42 micron and estimated staple length of 100-120 mm.

Chemicals (with suppliers noted) utilised for the treatment and testing were:
1. Potassium hydroxide (analytical reagent), Fisher Chemical;
2. Ethanol (96% v/v, food grade), Southern Grains;
3. Hydrogen peroxide (25% v/v, from 50% v/v technical grade), Jasol;
4. Sodium chloride (AR, ACS), Pronalys; and
5. Reverse osmosis (RO) water.

All treatments were carried out under ambient conditions and all testing was carried out under standard textile testing conditions (20° C. and 65% relative humidity).

All treatments were run with a fibre to liquor ratio of 1:40. A series of treatments, using 1.5% KOH/EtOH and 2% hydrogen peroxide, each having different ethanolic hydroxide treatment duration but the same (60 minute) hydrogen peroxide soaking period, were undertaken. The treatments used the following treatment times:
1. Control (untreated)
2. 8 minutes
3. 10 minutes
4. 12 minutes
5. 14 minutes
6. 16 minutes
7. 18 minutes
8. 20 minutes Each sample was then rinsed in RO water 5 times followed by drying at 40° C. for 30 minutes. The dry samples were place in labelled bags and then moved to a conditioned environment (with the bags unsealed) for a minimum of 48 hours prior to testing.

The Total Absorbency Capacity (ISO 11948:1-1998) was tested for each of the treatment samples. The sample size was 10 cm×10 cm (5 repeats for each variant).

Equipment: plastic mesh with square gaps (3 mm wide with 20 mm gaps), small sieve (pre weighed) and metal mesh to cover sieve and hold fibres in place.

The procedure standard method was as follows:
1) The dry conditioned product was weighed and placed in a sieve with metal mesh over top (to hold fibres in). The sieve was placed on a plastic mesh.
2) The mesh was lowered and sieved into a reservoir of sodium chloride solution (9 g/l, 1000 ml) and soaked for 5 minutes.
3) The grid was raised and sample cleared of the reservoir and left to drain for 5 minutes.
4) The sieve was removed, the lid taken off and weighed.
5) The difference between the dry and wet weights was calculated for 5× samples.
6) The average and standard deviation of results we calculated.

Figure 4:
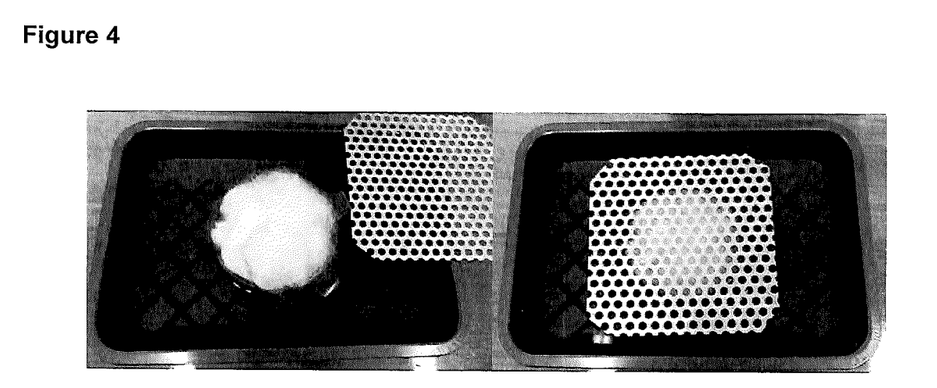
FIG. 4: shows an absorption experimental set up for the immersion stage of wool fibre substrate treatment.
Figure 5:
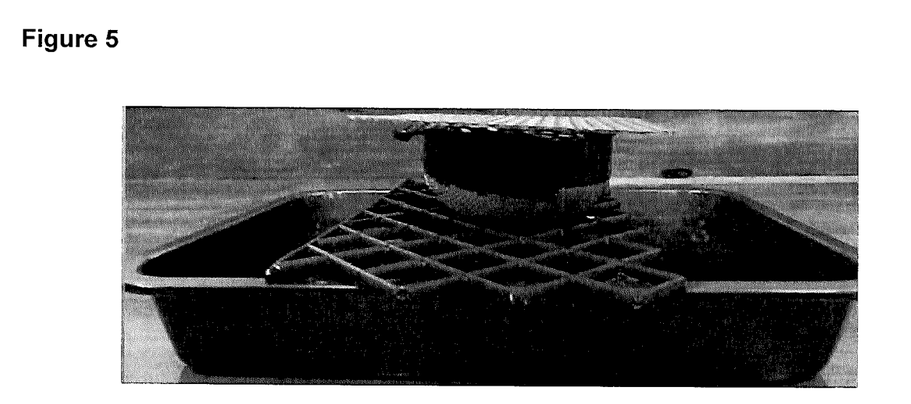
FIG. 5: shows an absorption experimental set up for the draining stage of wool fibre substrate treatment.

The experimental set-up was as shown in FIGS. 4 and 5.

A simulated sanitary absorbency experiment was also carried out. For each treatment time one additional sample was run with 250 ml of solution being poured evenly onto the sample (covered by metal mesh and on top of plastic mesh). This was allowed to soak for 5 minutes and then drained for 5 minutes before weighing. This technique was trialed as it represented the mode of action for sanitary or nappy (diaper) type products, in terms of comparable liquid volume application from above, rather than below.

Figure 6:
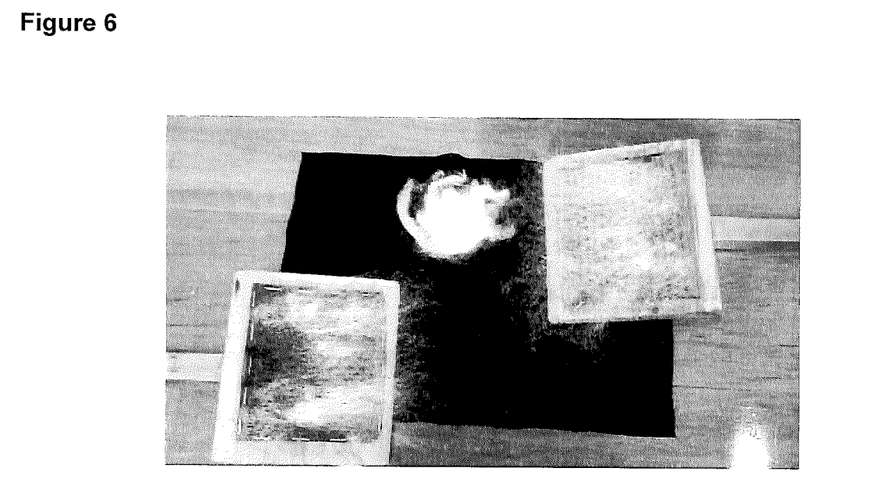
FIG. 6: shows the carded treated wool fibre substrate compared to a control sample.

A rectangle of conditioned, black, knitted wool fabric (25 cm×20 cm) was cut for each sample. This was then weighed before being spread out on a flat surface. A precisely weighed 5 g sample of each treatment duration was taken from the bulk material and then hand-carded in turn above a fabric piece. Each sample was carded in 4 portions with the portions being carded 10 times each. After carding, the fabric was reweighed and the loss of fibre during hand carding calculated. The carded fibre was bagged and labelled, and observations relating to ease of carding, fibre handle, bulk and appearance were recorded. FIG. 6 shows, for the control sample, the un-carded fibre, carded fibre and wool 'fibre catching' fabric.

Scanning electron microscopy (SEM) was used to gain information relating to the physical changes caused to the fibres during the treatment. SEM images samples by scanning them with a beam of electrons in a raster scan pattern. It allows materials to be viewed at very high magnification and allows investigation of fibre surface topography, composition and other properties. Samples were sputter coated from a gold/palladium leaf source to impart conductivity to the surface of the sample. Samples were studied using a JEOL JSM 7000F Field Emission Gun Scanning Electron Microscope. The microscope was operated at 10 kV and samples viewed at a working distance range of 11.3 mm-13.7 mm. Treated samples from 8 to 14 minutes inclusive do not have any significant signs of fibre damage in excess of what is normally found on scoured wool fibres (control sample). Once the treatment time reaches 16 minutes there are visible signs of damage to the surface of the fibres. In particular there is evidence of longitudinal 'wrinkles' forming on the fibres; these are more severe on the 18 and 20 minute samples. FIGS. 10-17 show the scanning electron microscopy images obtained from the different treatment samples.

Each fibre sample was evaluated in terms of how it felt when handled. There was a risk that the treatment could render the samples brittle and inflexible and this can be easily felt when the wool is handled. Since this test is subjective the samples were assessed by 3 volunteers and general comments were recorded. Both carded and un-carded samples were evaluated.

Results

Total Absorbency Capacity

The full set of results is provided in the following Tables 5-7.

TABLE 5

Total Absorbancy Capacity ISO 119848: 1-1998

| Treatment time | Sample number | Original sample mass (g) | Mass post immersion (g) | Difference in mass (g) | % Absorbency |
|---|---|---|---|---|---|
| 0 minutes | 1 | 4.06 | 28.13 | 24.07 | 593 |
|  | 2 | 4.00 | 26.69 | 22.69 | 567 |
|  | 3 | 4.08 | 17.15 | 13.07 | 321 |
|  | 4 | 4.26 | 18.02 | 13.76 | 323 |
|  | 5 | 4.17 | 27.63 | 23.46 | 562 |
| 8 minutes | 1 | 4.16 | 67.81 | 63.65 | 1530 |
|  | 2 | 4.06 | 76.49 | 72.43 | 1783 |
|  | 3 | 4.15 | 113.13 | 108.98 | 2627 |
|  | 4 | 4.13 | 96.34 | 92.21 | 2231 |
|  | 5 | 4.40 | 102.53 | 98.13 | 2229 |
| 10 minutes | 1 | 4.13 | 96.99 | 92.86 | 2251 |
|  | 2 | 4.11 | 102.76 | 98.65 | 2401 |
|  | 3 | 4.07 | 110.27 | 106.20 | 2606 |
|  | 4 | 4.04 | 110.40 | 106.36 | 2632 |
|  | 5 | 4.03 | 109.41 | 105.38 | 2617 |
| 12 minutes | 1 | 4.05 | 102.69 | 98.64 | 2436 |
|  | 2 | 4.09 | 106.34 | 102.25 | 2499 |
|  | 3 | 4.06 | 102.73 | 98.67 | 2429 |
|  | 4 | 4.04 | 100.49 | 96.45 | 2390 |
|  | 5 | 4.08 | 101.48 | 97.40 | 2387 |
| 14 minutes | 1 | 4.11 | 109.81 | 105.70 | 2570 |
|  | 2 | 4.03 | 104.72 | 100.69 | 2496 |
|  | 3 | 4.05 | 101.60 | 97.55 | 2406 |
|  | 4 | 4.05 | 98.79 | 94.74 | 2340 |
|  | 5 | 4.04 | 100.39 | 96.35 | 2385 |
| 16 minutes | 1 | 4.05 | 97.74 | 93.69 | 2314 |
|  | 2 | 4.04 | 68.71 | 84.67 | 2093 |
|  | 3 | 4.00 | 90.97 | 86.97 | 2174 |
|  | 4 | 4.08 | 101.01 | 96.93 | 2375 |
|  | 5 | 4.57 | 101.72 | 97.15 | 2128 |
| 18 minutes | 1 | 4.07 | 94.13 | 90.06 | 2213 |
|  | 2 | 4.12 | 94.48 | 90.36 | 2194 |
|  | 3 | 4.01 | 94.62 | 90.61 | 2257 |
|  | 4 | 4.03 | 89.08 | 85.05 | 2108 |
|  | 5 | 4.20 | 87.41 | 83.21 | 1983 |
| 20 minutes | 1 | 4.00 | 78.22 | 74.22 | 1854 |
|  | 2 | 4.15 | 82.60 | 78.45 | 1890 |
|  | 3 | 4.02 | 80.53 | 76.51 | 1901 |
|  | 4 | 4.13 | 81.98 | 77.85 | 1884 |
|  | 5 | 4.18 | 63.22 | 79.04 | 1891 |

TABLE 6

Total Absorbancy, average and standard deviation

| Treatment time | Average % absorbency | Standard deviation |
|---|---|---|
| 0 minutes | 473 | 139 |
| 8 minutes | 2080 | 429 |
| 10 minutes | 2502 | 169 |
| 12 minutes | 2428 | 45 |
| 14 minutes | 2440 | 92 |
| 16 minutes | 2217 | 122 |
| 18 minutes | 2151 | 108 |
| 20 minutes | 1884 | 18 |

TABLE 7

Simulated sanitary absorbancy

| Treatment time | Sample mass (g) | Mass post immersion (g) | Difference (g) | % Absorbency |
|---|---|---|---|---|
| Control | 5.04 | 19.70 | 14.66 | 291.11 |
| 8 minutes | 5.00 | 108.60 | 103.59 | 2070.02 |
| 10 minutes | 5.04 | 110.46 | 105.42 | 2092.79 |
| 12 minutes | 5.02 | 104.82 | 99.80 | 1988.34 |
| 14 minutes | 5.06 | 117.78 | 112.72 | 2229.83 |
| 16 minutes | 5.01 | 106.30 | 101.29 | 2022.45 |
| 18 minutes | 5.06 | 101.72 | 96.66 | 1910.46 |
| 20 minutes | 5.08 | 83.35 | 78.27 | 1542.24 |

Figure 7:
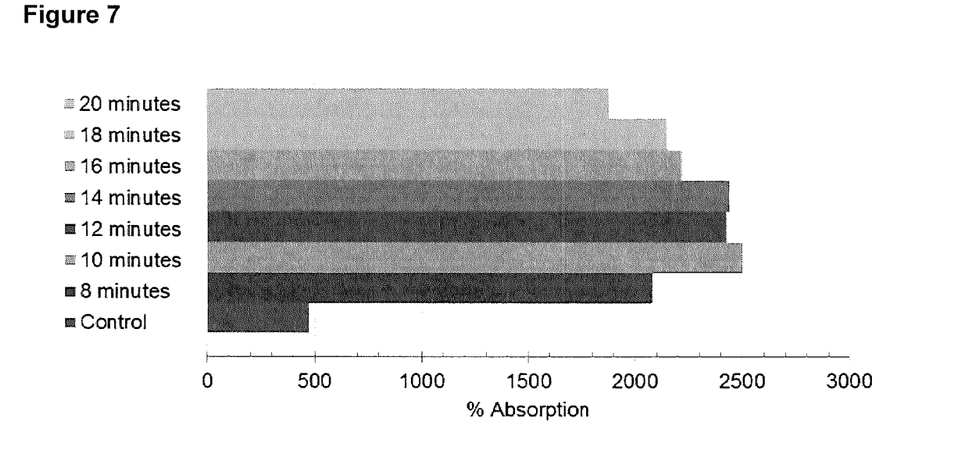
FIG. 7: shows the standard test method absorbency data of the treated wool fibre substrate.
Figure 8:
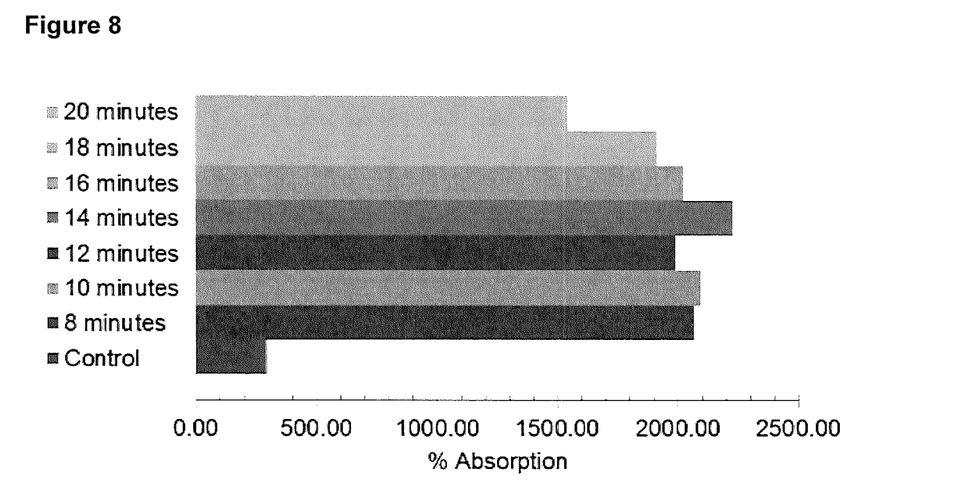
FIG. 8: shows the simulated sanitary absorbency of the treated wool fibre substrate.
Figures 8, 11:
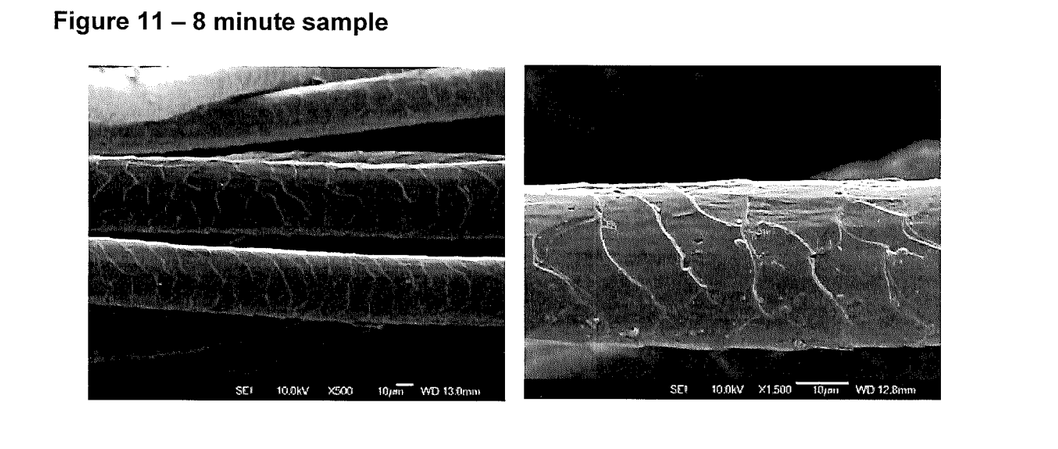
FIGS. 10-17: show low and high magnification scanning electron micrographs of 8 samples of treated wool fibre substrate.

The standard test method results are represented graphically in FIG. 7, with the simulated sanitary method represented in FIG. 8.

FIG. 7: Standard Test Method Absorbency Data

The average total absorbency capacity of the treated samples ranged from 1884-2502%, with the untreated samples having an average of 473%. The treated sample with the lowest absorbency was the 20 minute sample (longest duration). The standard deviation (see Table 6 above) was lowest for the 20 minute sample and highest for the 8 minute sample, with the remaining samples having similar standard deviations (including the control sample). This could be an indication of the levelness of the fibre treatment, with 8 minutes not allowing sufficient time for the liquor to penetrate and react evenly throughout the fibre bundles, meaning that samples taken from different regions of the treated material would behave differently.

FIG. 8: Simulated Sanitary Absorbency

The single test to simulate 'in use' conditions, based on a sanitary product, gave similar results to the standard test method (FIG. 8). The lowest treated sample absorbance was exhibited by the 20 minutes duration sample.

It was observed that, for both test methods, the 18 and 20 minute samples wetted out the most rapidly and the 8 and 10 minute samples the least rapidly. However all 7 treated samples wetted out without the need to apply pressure whilst the control sample tended to float on the surface of the solution until the mesh was placed on top of the sieve.

Figure 9:
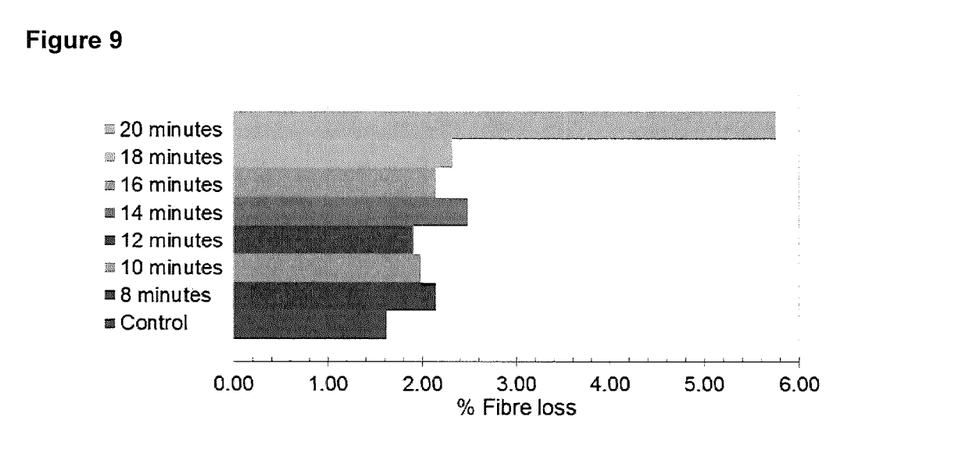
FIG. 9: shows the percentage fibre loss during hand carding of the treated wool fibre substrate.
Figure 10:
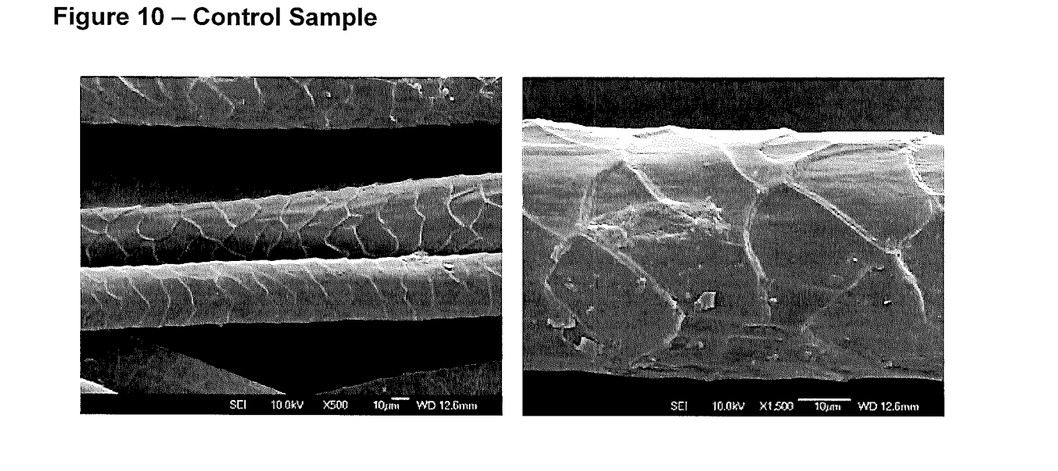
Figures 10, 12:
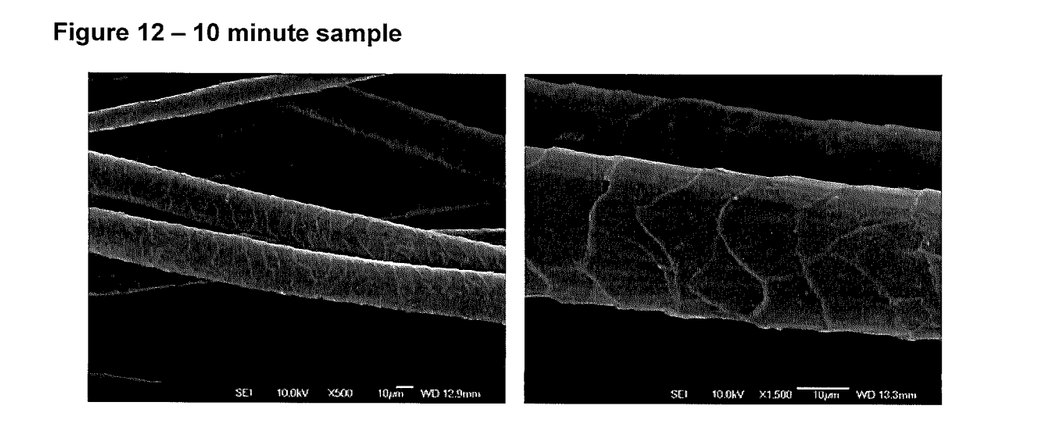
Figures 12, 13:
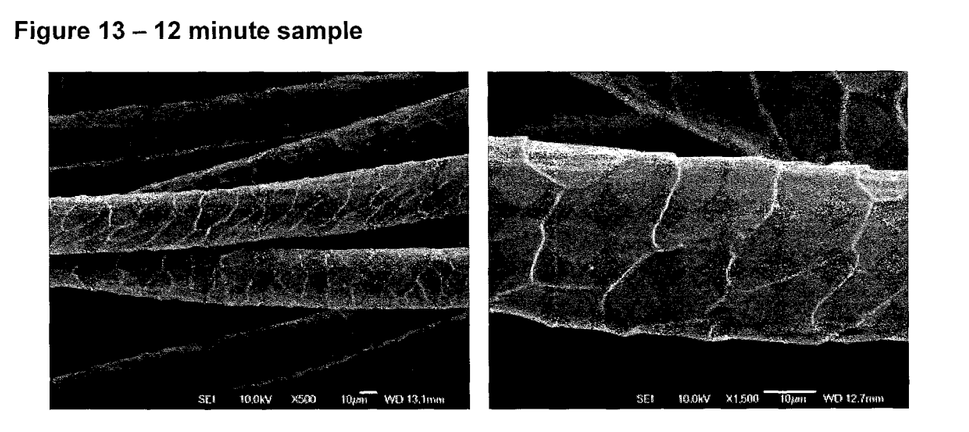
Figure 14:
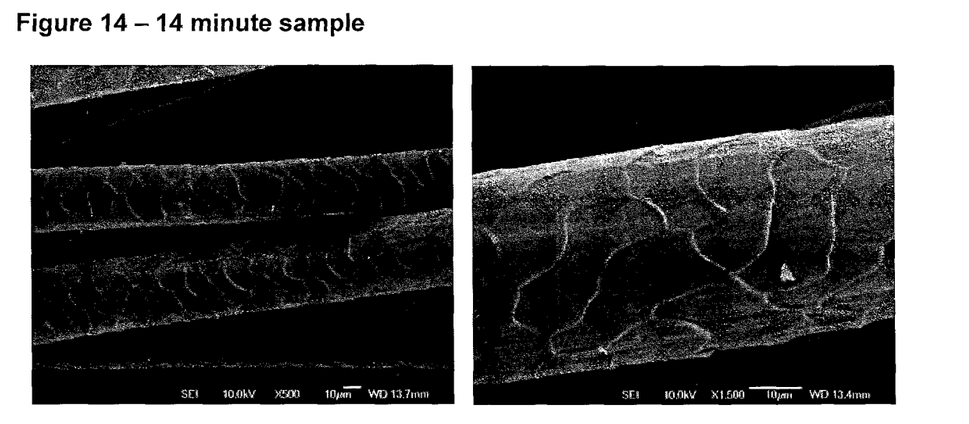
Figures 15, 16:
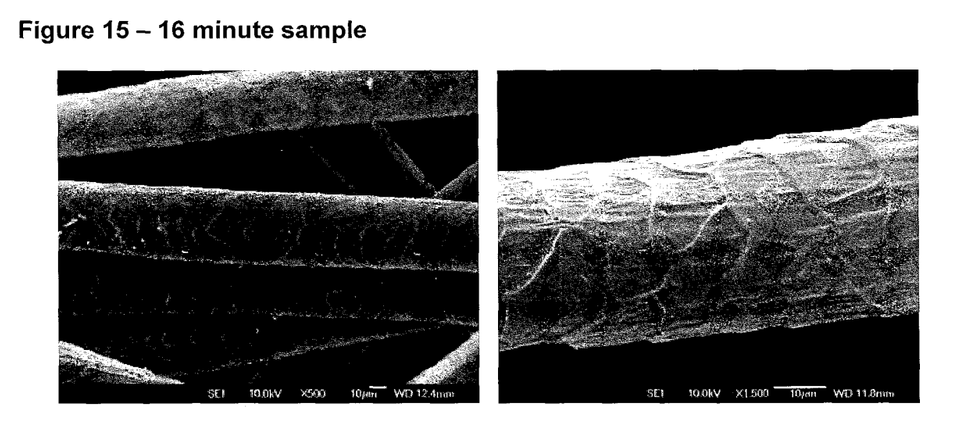
Figures 16, 18:
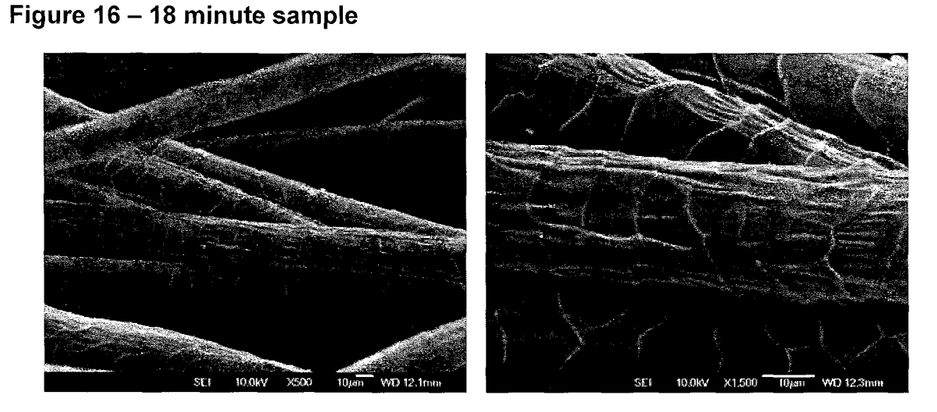
Figures 17, 20:
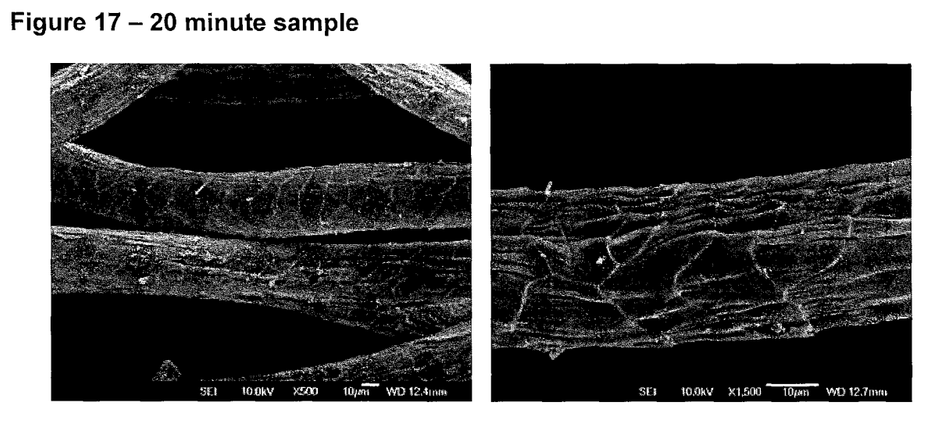

There is a risk that prolonging the duration of the treatment can substantially damage the fibres and render them unsuitable for any subsequent mechanical processing, which would be required in order to make yarns or fabrics from them. The hand carding trial allowed for a simple comparison to be made of the impact of the treatment duration on the fibres. Weakened fibres would be more easily broken and the resulting short fibres would tend to be lost during carding. The amount of fibre lost during hand-carding is represented in FIG. 9. The results clearly show that the majority of treatment durations experienced fibre loss at a level comparable with the control sample. The 20 minute sample lost almost 3 times more mass than the other samples which is indicative of a greater level of fibre damage.

The aim of this work was to determine the potential for scoured, loose wool fibre to be rendered super-hydrophilic via the treatment process of the invention and still be able to withstand gentle processing. The results from absorbency, hand-carding and SEM all demonstrated that as the treatment duration increased so did the damage to the fibres. Despite being the easiest to wet out with the test solution, at 20 minutes duration a decrease in the absorption results was observed. After examining the SEM images it became apparent that multiple longitudinal 'wrinkles' were present on the fibres which also appeared to be collapsing internally. It is possible that this has impacted the absorbency by providing channels that may facilitate absorption (by capillary action) but also allow the solution to drain off more easily, and also by reducing the capacity of the fibres to hold moisture internally (having partly collapsed). The lower apparent resilience of the fibres may also have reduced their ability to retain a volume of water between the fibres. Similar effects were observed on the SEM images for the 18 minute sample.

With regard to carding, the 20 minute sample was the only treated sample that exhibited appreciably larger fibre loss when compared to the control sample. It also had the driest handle and the lowest observed bulk and resilience properties. At the opposite end of the duration scale, the 8 minute sample had the largest standard deviation across its absorbency data. This suggests that the treatment may not be uniform throughout the sample. Taking into considering all of the data collected and observations made, a treatment time of 12-14 minutes is recommended for loose fibre. At this level the absorbency of the fibres is in the region of 2400%, the SEM images show minimal fibre damage (comparable with the control sample), the samples did not contain any consolidated areas and were easy to hand-card. The handle was observed to be drier than that of the control but the bulk and resilience were not adversely affected, although this was assessed by subjective trials only.

The present invention and its embodiments have been described in detail. However, the scope of the present invention is not intended to be limited to the embodiment described in the specification. Modifications and variations may be made to the disclosed embodiment without departing from the scope or essential characteristics of the present invention.

The invention claimed is:

1. A process for treating a wool substrate to increase the absorbency properties of the wool substrate, the process comprising:
   (i) a first reaction step of treating the wool substrate with an alcohol and alkali reaction mixture for a reaction time of about 8-30 minutes, wherein the alcohol and alkali reaction mixture comprises about 1-2% alkali mixed with alcohol, and wherein the alcohol and alkali reaction mixture comprises methanol, ethanol, propanol, butanol, or mixtures thereof, and potassium hydroxide, sodium hydroxide, or mixtures thereof; and
   (ii) a second reaction step of treating the resulting wool substrate obtained from the first reaction step with an aqueous oxidizing agent mixture for a reaction time of about 60-120 minutes, wherein the aqueous oxidizing agent mixture comprises about 2% hydrogen peroxide,
   wherein the process is carried out with a fibre to liquor ratio of at least 1:40,
   wherein the process increases the absorbency properties of the wool substrate as compared to an untreated wool substrate, and
   wherein the first reaction step and the second reaction step do not damage the wool substrate to render it unsuitable for mechanical processing for making wool yarns or wool fabrics or wool fabric products.

2. The process as claimed in claim 1 wherein the wool substrate used in the first reaction step is: (i) a chemically untreated nonwoven wool substrate; or (ii) a chemically untreated knop-infused nonwoven substrate.

3. The process as claimed in claim 1 wherein the wool substrate used in the first reaction step is selected from: (i) a needle punched wool nonwoven substrate comprising carded wool fibres and (ii) spunlaced (hydroentangled) wool nonwoven substrate comprising carded wool fibres.

4. The process as claimed in claim 1 wherein the wool substrate used on the first reaction step comprises loose wool fibres.

5. The process as claimed in claim 1 wherein the wool substrate is: (i) between about 100-1000 grams per square meter; or between about 200-600 grams per square meter.

6. The process as claimed in claim 1 wherein: (i) the alcohol is selected from methanol, ethanol, or mixtures thereof; and/or (ii) the alkali is potassium hydroxide.

7. The process as claimed in claim 6 wherein the alkali has a concentration of about 1.5% in the alcohol and alkali reaction mixture.

8. The process as claimed in claim 1 wherein the reaction time of the first reaction step is between about 10-30 minutes; or about 10 minutes.

9. The process as claimed in claim 1 wherein the reaction time of the first reaction step is about 12-14 minutes.

10. The process as claimed claim 1 wherein the reaction time of the second reaction step is about 60-90 minutes.

11. The process as claimed in claim 1 wherein the reaction time of the second reaction step is about 60 minutes.

* * * * *